(12) United States Patent
Praml (10) Patent No.: US 6,895,967 B2
(45) Date of Patent: May 24, 2005

(54) CONDOM WITH INFLATABLE PORTION

(76) Inventor: Scott Praml, 128 Sherman Ave. S, Berkley Heights, NJ (US) 07922

( * ) Notice: Subject to any disclaimer, the term of this patent is extended or adjusted under 35 U.S.C. 154(b) by 19 days.

(21) Appl. No.: 10/401,123

(22) Filed: Mar. 27, 2003

(65) Prior Publication Data
US 2004/0031491 A1 Feb. 19, 2004

Related U.S. Application Data (63) Continuation-in-part of application No. 10/218,552, filed on Aug. 14, 2002, now Pat. No. 6,651,668.

(51) Int. Cl.⁷ .................................................. A61F 6/04
(52) U.S. Cl. ........................ 128/844; 128/918; 604/347
(58) Field of Search ................................ 128/844, 842, 128/918; 604/347, 348, 349, 350, 351, 352, 353; 600/38

(56) References Cited

U.S. PATENT DOCUMENTS

| | | | |
|---|---|---|---|
| 4,281,648 A | 8/1981 | Rogers | 128/79 |
| 4,287,888 A | 9/1981 | Schwarz | 128/239 |
| 4,407,275 A | 10/1983 | Schroeder | 128/79 |
| 4,523,584 A | 6/1985 | Yachia et al. | 128/79 |
| 4,805,604 A * | 2/1989 | Spery | 128/844 |
| 4,961,734 A * | 10/1990 | Kassman | 604/349 |
| 5,074,314 A * | 12/1991 | Wilson | 128/844 |
| 5,163,449 A * | 11/1992 | van der Valk | 128/844 |
| 5,318,042 A * | 6/1994 | Gray | 128/844 |
| 5,377,692 A | 1/1995 | Pfeil | 128/844 |
| 5,469,863 A * | 11/1995 | Shah | 128/844 |
| 5,477,865 A * | 12/1995 | Broad, Jr. | 128/844 |
| 5,526,823 A * | 6/1996 | Wheeler et al. | 128/842 |
| 5,823,939 A | 10/1998 | Tsagarakis | 600/38 |
| 5,853,006 A * | 12/1998 | Metz | 128/844 |
| 5,885,205 A | 3/1999 | Kassman | 600/38 |
| 6,098,626 A | 8/2000 | Kim | 128/844 |
| 6,569,083 B1 * | 5/2003 | Kassman | 600/38 |

FOREIGN PATENT DOCUMENTS

DE           311726         4/1919

* cited by examiner

*Primary Examiner*—Fadi H. Dahbour
(74) *Attorney, Agent, or Firm*—Wolff and Samson PC (57) ABSTRACT

A condom having an inflatable portion is provided. The condom comprises an inner wall and an outer wall defining an annular chamber extending along a portion of the length of the condom. An air source, such as a handheld pump, is removably connected to a port which leads to an airway in the chamber for delivering air to a forward portion of the chamber. A plurality of vents are provided at a rearward end of the chamber for venting the air.

9 Claims, 8 Drawing Sheets

CONDOM WITH INFLATABLE PORTION

RELATED APPLICATIONS

This application is a continuation-in-part application of U.S. patent application Ser. No. 10/218,552 filed Aug. 14, 2002, now U.S. Pat. No. 6,651,668, the entire disclosure of which is expressly incorporated herein by reference.

BACKGROUND OF THE INVENTION

1. Field of the Invention

The present invention relates to a condom, and more specifically, to a condom having an inflatable portion to provide an enhanced sexual experience.

2. Related Art

In an era with sexually transmitted diseases (STDs) and strong concern about family sizes, birth control is practiced in various forms by a large segment of the population. Condoms are a widely used birth control device that not only provides contraception, but also serves to reduce the spread of STDs. Condoms have been fabricated from various materials and have been structurally modified to provide increased sexual pleasure. An example of such an enhancement is the ribbed condom, wherein ribs are provided along the length of the condom body to provide additional stimulus to the female. Additionally, materials such as lambskin have been used to form the condom body, in order to provide increased sensitivity to the male. However, these enhancements generally provide only relatively moderate stimulation.

Accordingly, what is desirable, but has not yet been provided, is a condom that can provide for an enhanced sexual experience.

SUMMARY OF THE INVENTION

The present invention relates to a condom with an inflatable portion. The condom has an inner wall and an outer wall defining an annular chamber. The chamber has a base portion and a top portion, the top portion located rearward of the tip of the condom and the base portion located forward of the open end of the condom. The base portion includes a port connected to an internal airway that extends along the length of the annular chamber and terminates proximate to the top portion of the chamber. An air source removably connectable with the port allows for the introduction of a burst of air into the chamber via the port and the internal airway. The air travels along the internal airway and into the annular chamber, allowing same to be inflated at desired times to provide an enhanced experience. A plurality of air vents disposed about the base portion of the annular chamber allow for quick deflation of the chamber.

The present invention includes a handheld pump having a flexible tube with a nozzle at the end thereof. The nozzle is received by the port of the condom. The pump and associated flexible tube can be disconnected from the condom, and re-used with another condom. The condom can be fabricated using standard manufacturing processes, rolled up and stored in a small package (as is done with conventional condoms), and then removed from the package and used as a conventional condom. Moreover, the outer wall of the condom can include ribs for providing an enhanced sexual experience.

In an embodiment of the present invention, the inflatable portion extends along the length of the condom and is attached at a forward end to the inner wall, rearward of the tip portion of the condom. The rearward end of the inner wall is attached to the base portion (open end) of the condom. The base portion includes a plurality of air vents for allowing air to escape from the inflatable portion. Additionally, the inlet port of the internal airway is located on the base portion.

BRIEF DESCRIPTION OF THE DRAWINGS

These and other important features and advantages of the present invention will be apparent from the following Detailed Description of the Invention taken in connection with the accompanying drawings in which.

DETAILED DESCRIPTION OF THE INVENTION

The present invention relates to a condom with an inflatable portion in the form of an annular chamber defined by an inner wall and an outer wall. A port at the base of the chamber is connected to an internal airway that extends along the length of the chamber and allows for the delivery of air into the annular chamber, so that the chamber can be inflated at desired times to provide an enhanced experience. A plurality of air vents are disposed about the base portion of the annular chamber, to allow for quick deflation of the annular chamber. An air source, such as a handheld pump, is removably connected to the port for inflating the chamber. The condom operates as a standard prophylactic, can be stored in a rolled configuration in a small package, and can be applied for use and worn in the same manner as a conventional condom.

Figure 1:
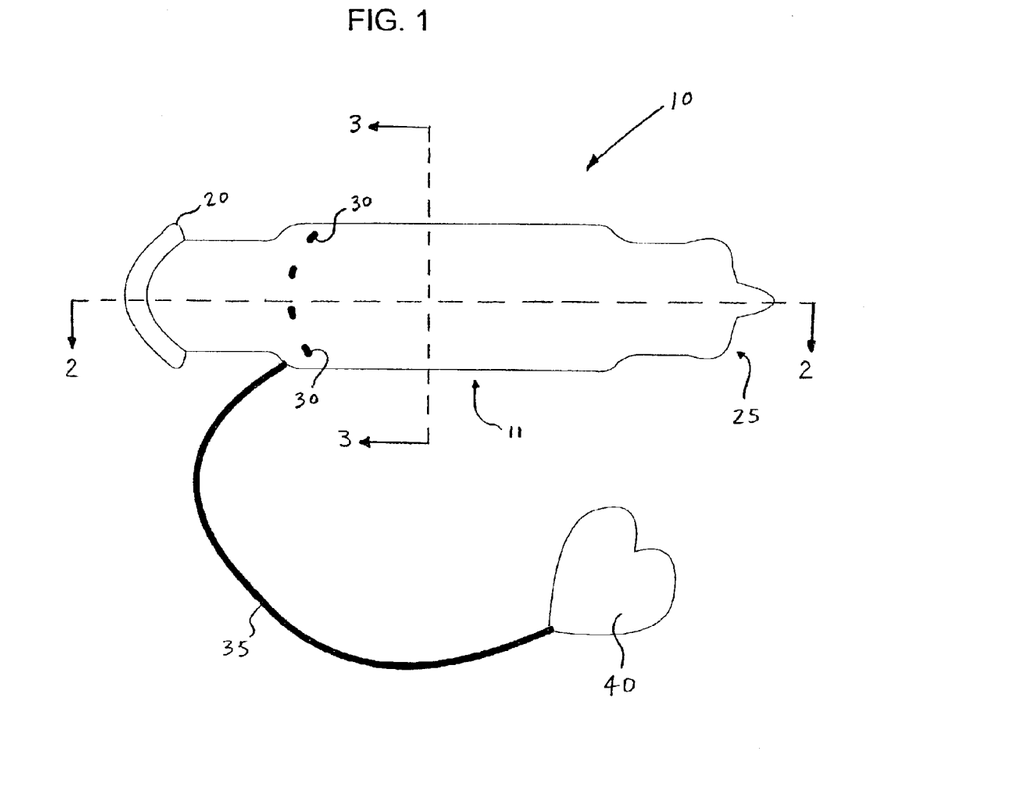
FIG. 1 is a side view showing the condom of the present invention, connected to a handheld pump.

FIG. 1 is a side view showing the inflatable condom of the present invention, indicated generally at 10 and shown connected to a handheld pump 40 via tube 35. The condom 10 includes a base 20, a tip 25, and an inflatable portion 11. The inflatable portion 11 can be selectively inflated at desired times by pumping handheld pump 40, to provide enhanced sexual pleasure. A plurality of air vents 30 are disposed about the base of the inflatable portion 11 of the condom 10. When the pump 40 is squeezed, air is injected from the pump 40, through the tube 35, and into the condom 10, inflating the inflatable portion 11. The air then exits through the plurality of air vents 30, allowing quick deflation of inflatable portion 11.

Importantly, the condom 10 of the present invention can be manufactured using known processes (i.e., processes utilized to produce conventional condoms). Further, the hand pump 40 and tube 35 can be disconnected from the condom 10 for storage and/or later use with another condom. The condom 10 can be rolled up and stored in a small package, as is done with conventional condoms. Further, the condom 10 can be removed from such a package and used in the same manner as a conventional condom. The tube 35 of handheld pump 40 is attached to the condom 10, to allow inflation thereof. The condom 10 can be manufactured from latex rubber, or any other suitable material known in the art, and can include ribs disposed along the length thereof to provide additional stimulus.

Figure 2:
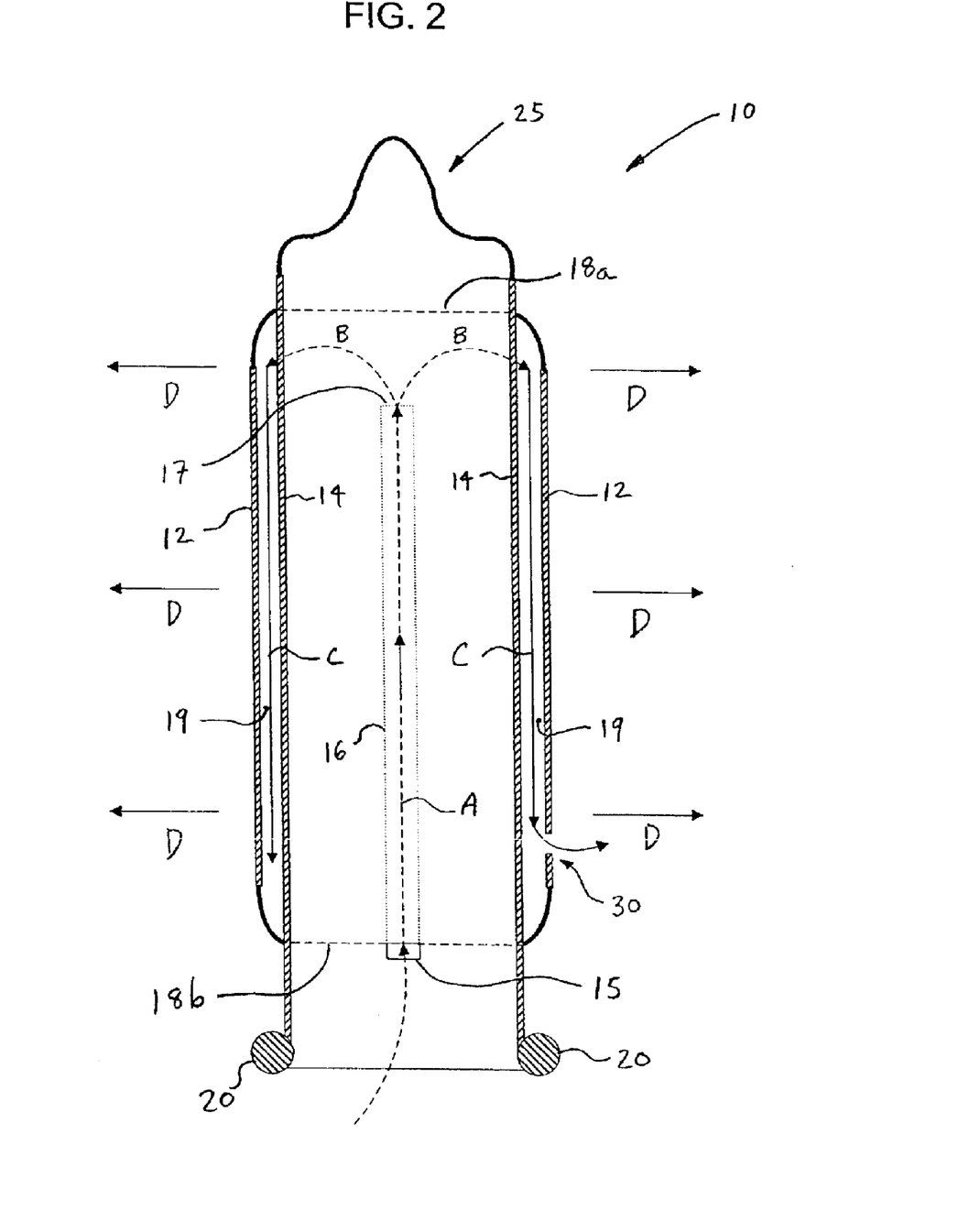
FIG. 2 is a cross-sectional view of the condom of the present invention, taken along the line 2—2 of FIG. 1.

FIG. 2 is a cross-sectional view of the condom 10 of the present invention, taken along the line 2—2 of FIG. 1. The condom 10 comprises a flexible outer wall 12 and a flexible inner wall 14, both of which are connected together at one end towards the tip 25, and at the other end forward of the base 20. Preferably, the base 20, the inner wall 14, and the tip 25 are of a uniform construction, and the outer wall 12 is attached circumferentially to inner wall 14 towards tip 25 along seam 18a, at the forward edge of the chamber, and near base 20 along seam 18b, at the base of the chamber. Alternatively, the outer wall 12 can be attached directly to the base 20 of the condom. The outer wall 12 and inner wall 14 define an annular chamber 19, which can be inflated at desired times to provide an enhanced experience. The condom 10 is worn in the same fashion as a conventional condom.

The condom 10 of the present invention preferably includes a port 15 that is connected to an internal airway 16 near the base of the chamber. The internal airway 16 preferably extends along the length of annular chamber 19, and is connected between the outer wall 12 and the inner wall 14. Air introduced at the port 15 is fed into the chamber 19 by the airway 16, to inflate the chamber 19.

Thus, as can be seen in FIG. 2, air introduced at port 15 travels along the airway 16, in the direction indicated by arrow A. Then, the air exits the internal airway 16 at aperture 17, where it disperses into the annular chamber 19 in the direction indicated generally by arrows B. The air fills the annular chamber 19 along the general path indicated by arrow C, inflating the annular chamber 19 and causing outer wall 12 to expand outward in the general direction indicated by arrows D. The plurality of vents 30 at the base of the chamber allow the air pumped into the annular chamber 19 to be released after the annular chamber 19 has been inflated.

Figure 3:
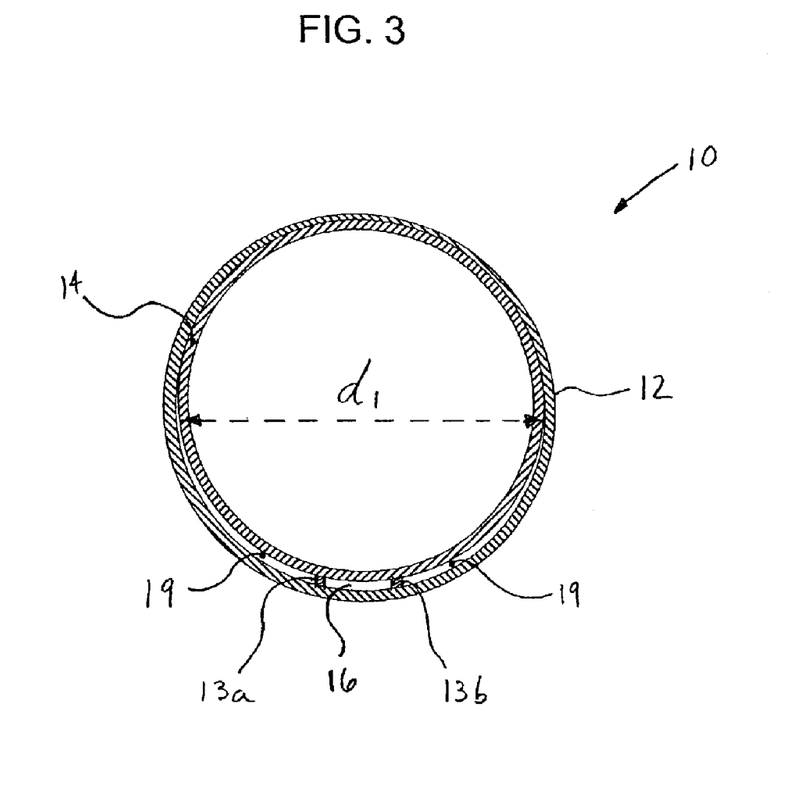
FIG. 3 is cross-sectional view of the condom of the present invention, taken along the line 3—3 of FIG. 1

FIG. 3 is cross-sectional view of the condom 10 of the present invention, taken along the line 3—3 of FIG. 1. When the annular chamber 19 of the condom 10 of the present invention is deflated, as shown in FIG. 3, the outer wall 12 rests against the inner wall 14, and has an initial diameter $d_1$. In a preferred embodiment of the present invention, walls 13a and 13b are connected between outer wall 12 and inner wall 14 to define the internal airway 16, and are sufficiently flexible to allow the internal airway 16 to expand when the annular chamber 19 is inflated. Further, the walls 13a and 13b are preferably manufactured from the same material as outer and inner walls 12 and 14, such as latex rubber.

Figure 4:
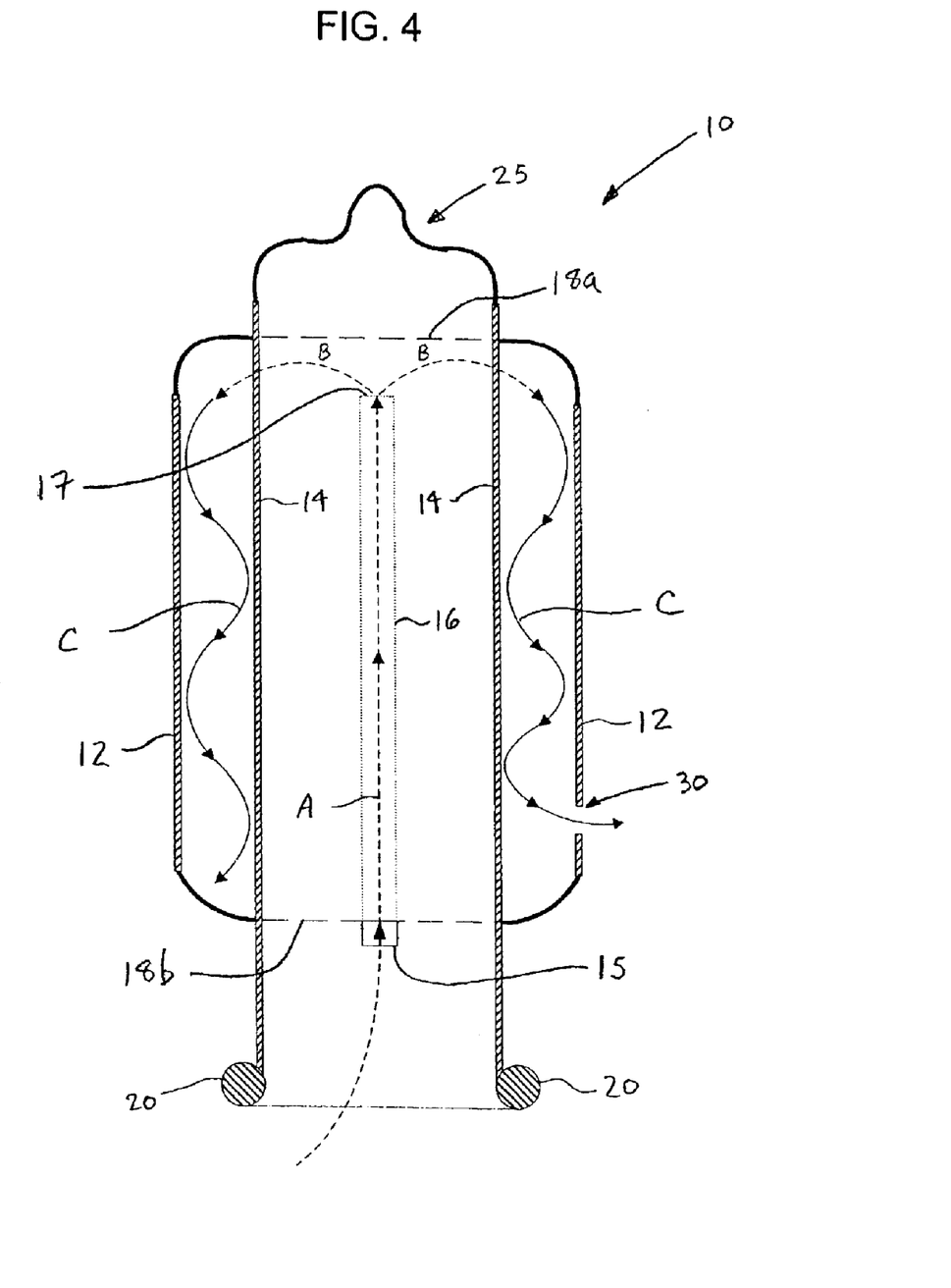
FIG. 4 is a cross-sectional view of the condom of the present invention, showing the annular chamber inflated and the outer wall expanded.

FIG. 4 is a cross-sectional view of the condom 10 of the present invention, showing the annular chamber 19 inflated and the outer wall 12 expanded. As mentioned previously, the annular chamber 19 of the condom 10 can be selectively inflated, causing the outer wall 12 to expand in diameter. This has the effect of providing additional stimulus during use for the wearer and/or partner. Thus, as shown in FIG. 4, when one or more bursts of air have been introduced into port 15 of the condom 10, the air travels through the internal airway 16 via path A, exits through the aperture 17 of the internal airway 16 along paths B, and flows into the annular chamber 19 along paths C. The air introduced into the annular chamber 19 causes the outer wall 12 to briefly expand away from inner wall 14. The bursts of air can be provided by the wearer or a partner by squeezing the handheld pump 40 of FIG. 1, or by activating any external air source connected to port 15. The plurality of air vents 30 allow the air accumulated in the annular chamber 19 to escape, thereby deflating same. This allows for the chamber to be repetitively inflated and deflated at desired times.

Figure 5:
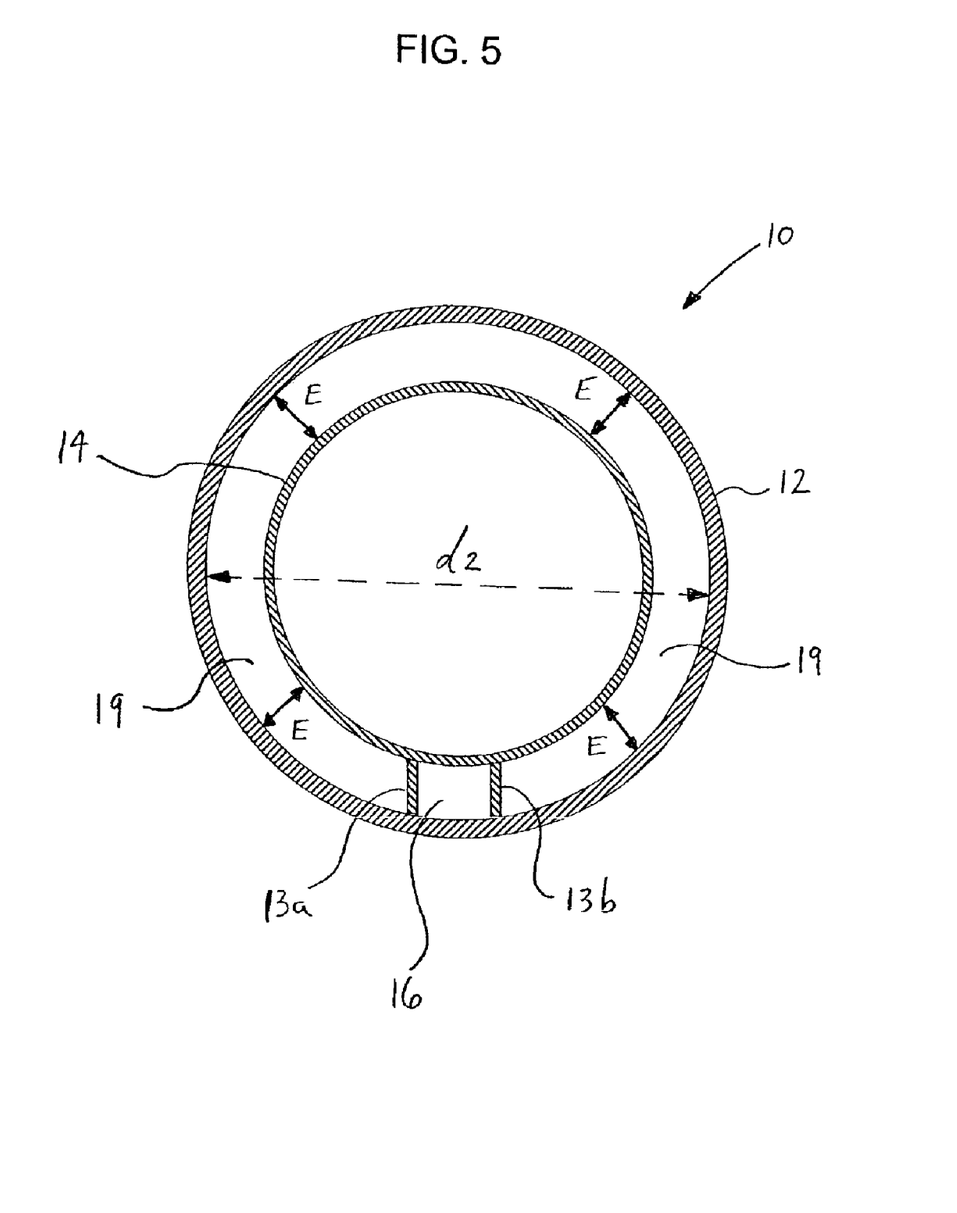
FIG. 5 is a cross-sectional view of the condom of the present invention, showing in greater detail the annular chamber when inflated.

FIG. 5 is a cross-sectional view of the condom 10 of the present invention, showing in greater detail the annular chamber 19 when inflated. When air has been introduced via internal airway 16 into the annular chamber 19, it accumulates therein and causes an increase in pressure. This increase in pressure stretches the outer wall 12 away from inner wall 14, along the direction indicated generally by arrows E, thereby increasing the diameter of outer wall 12 to diameter $d_2$, which is preferably larger than the uninflated diameter $d_1$ shown in FIG. 3. The walls 13a and 13b of the internal airway 16 can expand to accommodate the inflation. After the annular chamber has been inflated, the annular chamber deflates through air vents 30. The annular chamber can then be re-inflated as desired.

Figure 6:
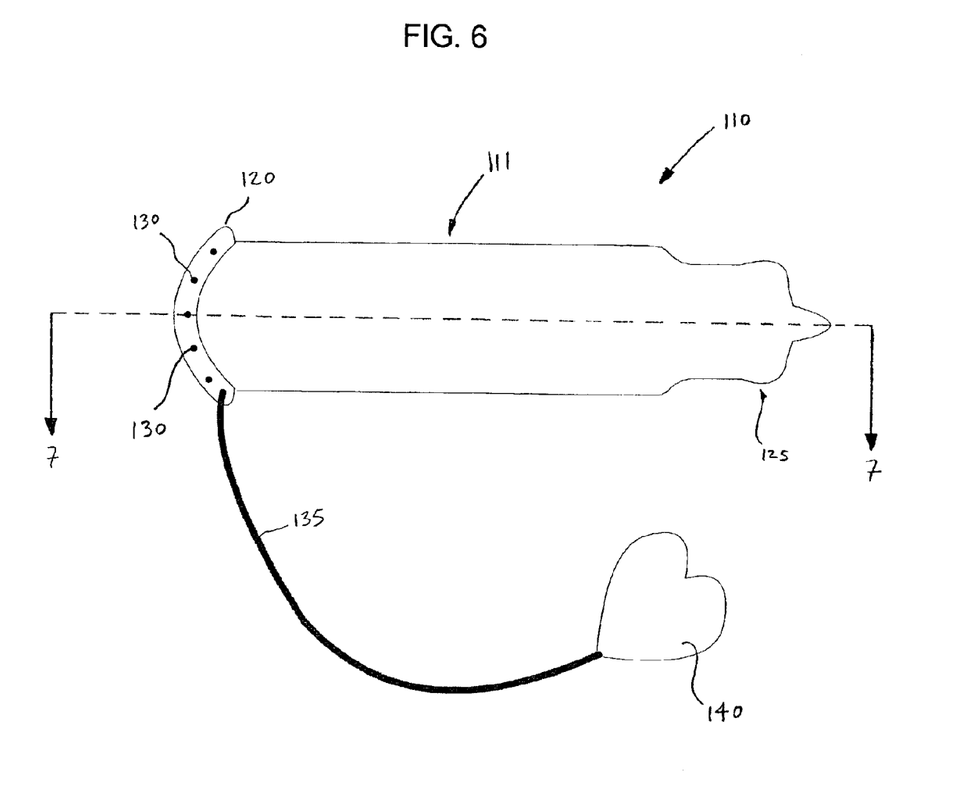
FIG. 6 is a side view of another embodiment of the condom of the present invention, wherein the inflatable portion is attached at a rearward end to the base portion of the condom, and the plurality of air vents and an air inlet port is located on the base portion.

FIG. 6 is a side view showing another embodiment of the inflatable condom of the present invention, indicated generally at 110, wherein the inflatable portion of the condom extends to the base portion (open end) of the condom, and the plurality of air vents and the inlet port is located on the base portion. The condom 110 includes a base portion 120, a tip 125, and an inflatable portion 111. The inflatable portion 111 extends along the length of the condom 110, beginning at a forward end near the tip 125 and ending at a rearward end to the base portion 120 (open end) of the condom 110. A plurality of air vents 130 are disposed about the base portion 120. The inflatable portion 111 can be selectively inflated through the use of a hand pump 140 connected to the base portion 120 as will be described.

Figure 7:
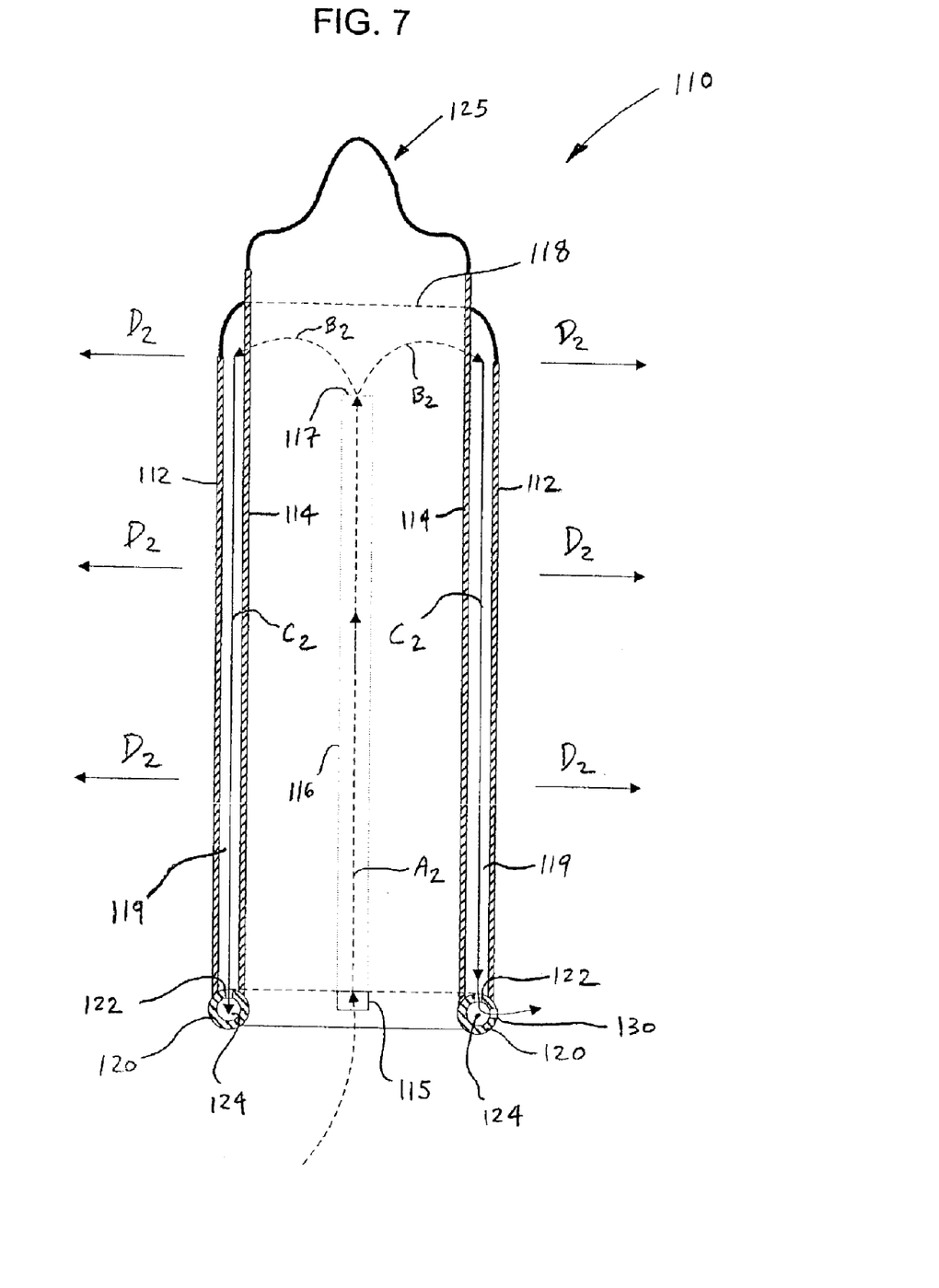
FIG. 7 is a cross-sectional view of the condom of the present invention, taken along the line 7—7 of FIG. 6.

FIG. 7 is a cross-sectional view of the condom 110 of the present invention, taken along the line 7—7 of FIG. 6. The condom 110 comprises a flexible outer wall 112 and a flexible inner wall 114, both of which are connected together at one end towards the tip 125. The rearward ends of the outer wall 112 and the inner wall 114 are attached to the base portion 120. The base portion 120, the inner wall 114, and the tip 125 could be of a uniform construction, and the outer wall 112 attached circumferentially to inner wall 114 towards tip 125 along seam 118, at the forward edge of the chamber, and to the base portion 120 at its rearward edge. The outer wall 112 and inner wall 114 define an annular chamber 119.

The base portion 120 comprises an annular cavity 124 with a plurality of air vents 130 thereabout. The base portion 120 includes apertures 122 for fluid communication between the annular cavity and the annular chamber. A port 115 on the base portion 120 is connected to an internal airway 116 extending through the base portion 120 and along the length of annular chamber 119. The internal airway 116 is connected between the outer wall 112 and the inner wall 114. Air introduced at the port 115 is fed into the chamber 119 by the airway 116, to inflate the chamber 119. Air introduced at port 115 travels along the airway 116, in the direction indicated by arrow $A_2$. Then, the air exits the internal airway 116 at forward aperture 117, where it disperses into the annular chamber 119 in the direction indicated generally by arrows $B_2$. The air fills the annular chamber 119 along the general path indicated by arrows $C_2$, inflating the annular chamber 119 and causing outer wall 112 to expand outward in the general direction indicated by arrows $D_2$. Air in the annular chamber 119 travels into an annular cavity 124 of the base portion 120 via apertures 122, where it escapes from the interior cavity 124 of the base portion 120 via plurality of apertures 130.

Figure 8:
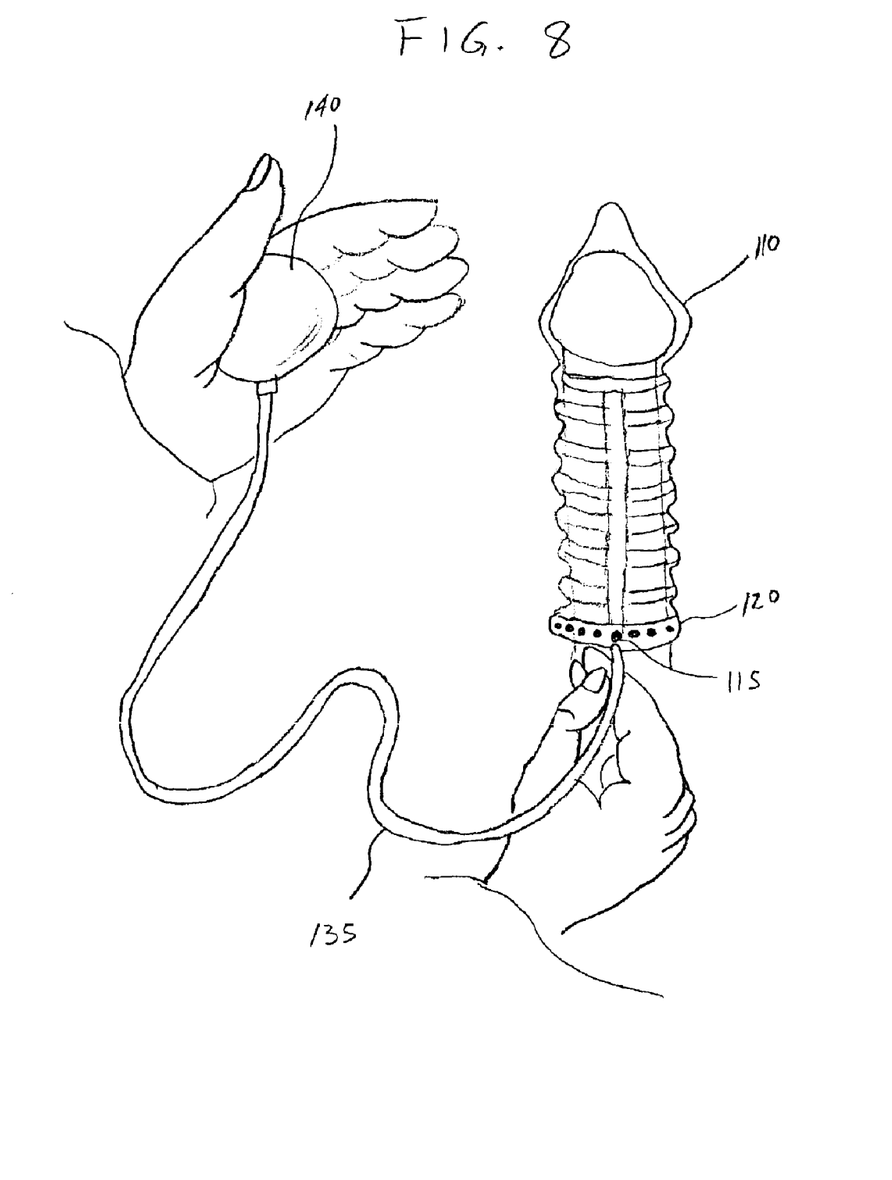
FIG. 8 is a perspective view showing the condom of the present invention in use on a penis.

FIG. 8 is a perspective view showing the condom 110 of the present invention in use on a penis. The condom 110 is applied in the same fashion as a conventional condom (e.g., unpackaged and rolled onto the penis). The free end of tube 135 attached to a hand pump 140 is connected to the inlet port 115 on the base portion 120 of the condom 110. Once connected, the hand pump 140 can be selectively pumped to inflate the annular chamber of the condom at desired times.

Having thus described the invention in detail, it is to be understood that the foregoing description is not intended to limit the spirit and scope thereof. What is desired to be protected by Letters Patent is set forth in the appended claims.

What is claimed is:

1. A condom having an inflatable portion, comprising:

a base portion, an inner wall, and a tip;

an outer wall surrounding a portion of the inner wall, the outer wall connected at a forward end to the inner wall, and at a rearward end to the base portion, to define an annular chamber between the inner and outer walls extending from a forward area near the tip to the base portion;

an airway extending from the base portion and into the annular chamber to the forward end of the annular chamber for delivering air into the forward end of the chamber;

a plurality of apertures for airflow between the annular chamber and the base portion; and a plurality of air vents disposed on the base portion for allowing airflow from the base portion to the atmosphere.

2. The condom of claim 1, further comprising an air source removably connected to the airway for inflating the annular chamber.

3. The condom of claim 2, wherein the air source comprises a handheld pump connected to the airway by a tube.

4. The condom of claim 1, wherein the inner wall, the outer wall, and the airway comprise latex rubber.

5. The condom of claim 1, wherein the inner wall, the outer wall, and the airway can be rolled up for packaging.

6. The condom of claim 1, wherein the outer wall further comprises a plurality of ribs disposed lengthwise along the outer wall.

7. The condom of claim 1, further comprising an inlet port connected to the airway at the base portion.

8. The condom of claim 1, wherein the base portion comprises an annular cavity for receiving air from the annular chamber.

9. The condom of claim 8, wherein air in the annular cavity exits through the plurality of air vents disposed about the base portion.

* * * * *